(12) United States Patent
Wang et al.

(10) Patent No.: US 8,003,395 B2
(45) Date of Patent: Aug. 23, 2011

(54) NON-SIGNAL IMIDAZOLE REAGENTS FOR MASS SPECTROMETRY ANALYSIS OF PHOSPHOMONOESTERS

(75) Inventors: Poguang Wang, Westborough, MA (US); Guodong Li, Malden, MA (US); Roger W. Giese, Quincy, MA (US)

(73) Assignee: Trace Bio Analytics, LLC, Boston, MA (US)

( * ) Notice: Subject to any disclaimer, the term of this patent is extended or adjusted under 35 U.S.C. 154(b) by 212 days.

(21) Appl. No.: 11/922,732

(22) PCT Filed: Jun. 21, 2006

(86) PCT No.: PCT/US2006/024059
§ 371 (c)(1), (2), (4) Date: May 11, 2009

(87) PCT Pub. No.: WO2007/002135
PCT Pub. Date: Jan. 4, 2007

(65) Prior Publication Data
US 2009/0215185 A1    Aug. 27, 2009

Related U.S. Application Data

(60) Provisional application No. 60/692,704, filed on Jun. 21, 2005.

(51) Int. Cl.
*G01N 33/00* (2006.01)

(52) U.S. Cl. ............................. 436/86; 435/6; 436/518
(58) Field of Classification Search .................. None
See application file for complete search history.

(56) References Cited

U.S. PATENT DOCUMENTS

| 5,512,486 A | 4/1996 | Giese et al. |
| 5,605,798 A | 2/1997 | Köster et al. |
| 2004/0157344 A1 | 8/2004 | Wang et al. |

OTHER PUBLICATIONS

Flarakos, J. A deoxynucleotide derivatization methodology for improving LC-ESI-MS detection. *Analytical Chemistry*, vol. 77, No. 8, pp. 2373-2380; 2005.
Lan, Zhang-Hua et al. Matrix-assisted laser desorption/ionization mass spectrometry of deoxynucleotides labeled with an IMI dye. *Rapid Comm. Mass. Spectrom*, vol. 13, pp. 1454-1457; 1999.
Wang, P. et al. Phosphate-specific fluorescence labeling under aqueous conditions. *Analytical Chemistry*, vol. 65, No. 23, pp. 3518-3520; 1993.

*Primary Examiner* — Yelena G Gakh
*Assistant Examiner* — David Weisz
(74) *Attorney, Agent, or Firm* — Alan W. Steele; Foley Hoag LLP

(57) ABSTRACT

Analytical chemical reagents termed non-signal imidazoles and a method for their use that provide a host of advantages for analysis of phosphomonoesters are described. The method and compounds of the invention provide a host of advantages for the analysis of phosphomonoester-containing compounds, namely characteristic, multi-analyte detection with high sensitivity and specificity of known and unknown phosphomonoester-compounds simultaneously.

13 Claims, 10 Drawing Sheets

1: methyl-C (533.155, 1 ppm), 2: methyl-U (534.139, 7 ppm), 3: methyl-A (557.166 2 ppm), 4: methyl-G (573.161, 5 ppm), 5: dimethyl-G (587.177, 1 ppm), 6: i6A (611.213, 2 ppm), 7:m6t6A, hn6A (702.204, 6 ppm)

PSD of the labeled phospho-peptide shows that the Tag is on phosphate site, and parent ion is much more stable even with collision gas on.

NON-SIGNAL IMIDAZOLE REAGENTS FOR MASS SPECTROMETRY ANALYSIS OF PHOSPHOMONOESTERS

CROSS REFERENCE TO RELATED APPLICATIONS

This application claims priority under 35 U.S.C. §119(e) of U.S. Provisional Application No. 60/692,704, filed Jun. 21, 2005, entitled "ULTRASENSITIVE MASS DETECTION OF ORGANOPHOSPHATES," the entire disclosure of which is hereby incorporated by reference.

STATEMENT REGARDING FEDERALLY SPONSORED RESEARCH OR DEVELOPMENT

N/A

BACKGROUND OF THE INVENTION

Phosphomonoester-containing compounds are an important group to be able to analyze with accuracy and sensitivity because many bioactive molecules fall into this class. These molecules include phosphomonoester forms of nucleosides (e.g., ribonucleotides, deoxyribonucleotides, dideoxyribonucleotides), nucleoside di- and tri-phosphates, deoxynucleoside di- and tri-phosphates, dinucleotides, trinucleotides, oligonucleotides, lipids, oligosaccharides, amino acids, sugars, peptides, metabolites and drugs. High performance analysis is required because of the multiplicity, diversity, low concentrations, and adsorptive nature of many of these phosphomonoesters, making their analysis difficult.

Aryl groups such as phenyl, pyridyl and naphthyl are common parts of organic compounds. Often an aryl group in a compound is substituted with a group such as bromo, chloro, alkyl (such as methyl), alkoxy (such as methoxy), deutero or amide. This substitution modifies the chemical or physical properties of the compound to one degree or another. More than one substitutent may be present on an aryl group.

Mass spectrometry is an important technique for analyzing many chemical substances. At its best, it provides characteristic multi-analyte detection with high sensitivity and specificity. However, rarely are these advantages brought together in a single method. In general, the sensitivity of mass spectrometry is analyte and sample dependent, and varies with the conditions in the mass spectrometer. Even when conditions are optimized for each analyte of interest, and each analyte is detected under the best possible conditions, responses can vary widely for different analytes. Different analytes also tend to fragment to different degrees in the mass spectrometer. The most intense fragment may come from only a small part of the overall structure of a compound, providing little structural characterization. This failure of mass spectrometry to achieve its full analysis potential exists for all forms of mass spectrometry. This includes the common techniques of matrix assisted laser desorption ionization mass spectrometry (MALDI-MS), and electrospray ionization mass spectrometry (ESI-MS), including MS/MS forms of these techniques. Unfortunately, phosphomonoester compounds are among the worst in their present capability of being analyzed with high performance by mass spectrometry.

Stable isotope reagents, in which a chemical reagent is enriched in a stable isotope such as deuterium, are widely used in mass spectrometry. In one use, a known amount of a stable isotope form of the analyte is added to a sample to provide a more accurate analysis of this sample based on the principle of isotope dilution. In another use, corresponding covalent labeling reagents as an isotope duo (one ordinary and one isotope-enriched) are used separately so that the target analyte is labeled in one sample with an ordinary reagent, and the same analyte in the second sample is labeled with the corresponding stable isotope reagent. The samples then can be combined prior to subsequent cleanup steps before analysis by mass spectrometry, revealing the relative amount of the target analyte in the two samples. In a third use, a given sample is reacted with a combined isotopic duo in order to convert an analyte into a pair of products that give a mass-distinctive, split signal in the mass spectrometer to enhance specificity. Stable isotope forms of test substances are also used in mass spectrometry to sort out fragmentation pathways and identify exchangeable atoms.

The sensitivity for detection of phosphomonoester compounds can be increased and made relatively uniform by labeling the compounds with a pre-existing signal group such as a fluorescent dye or radioisotope that inherently provides intensive detection properties by the corresponding detection technique for the signal group employed. For example, Giese and Wang (U.S. Pat. No. 5,512,486) introduced imidazole reagents containing pre-existing signal groups for labeling of phosphomonoester compounds to improve detection sensitivity by the designated detection technique for the pre-existing signal group. One of these reagents, containing a pre-existing fluorescent signal group, was used to convert a nucleotide into a corresponding fluorescent phosphorimidazolide, and the latter compound then was detected by fluorescence detection. The structure of the compound was confirmed by MALDI-TOF-MS. However, high sensitivity was not demonstrated by this MS technique, since the smallest amount of fluorescent phosphorimidazolide detected in the instrument was 30 picomoles. High specificity was not demonstrated since there was no isotopic duo. Multi-analyte detection was not encouraged, since several fragmentation peaks were formed by the fluorescent phosphorimidazolide product. There was no evidence that different nucleotides could give a similar response under a single set of MS conditions.

Creation of a signal group by combining an analyte with a non-signal chemical derivatization reagent is known in the field of detection by fluorescence. For example, fluorescamine and o-phthalaldehyde non-signal reagents can be reacted with amine-bearing compounds to form fluorescent products.

Characteristic, multi-analyte analysis with high sensitivity and specificity is important for phosphomonoesters because of the great number and diversity of bioactive compounds in this class. It is important to simultaneously detect known and unknown phosphomonoesters, since not all bioactive phosphomonoester compounds may have been discovered or identified, and their role needs to be sorted out both independently and relative to known phosphomonoesters. High sensitivity is critical especially for human samples which are often limited in amount, and further may have a low concentration of phosphomonoesters. High specificity is important in the analysis of phosphomonoesters to avoid false positive and false negative results.

BRIEF SUMMARY OF THE INVENTION

This invention is directed to analytical methodology, reagents and products that provide characteristic, multi-analyte analysis of phosphomonoester-containing compounds with high sensitivity and specificity by mass spectrometry. A signal group capable of furnishing this set of detection properties is created by covalently labeling the phosphomonoester group of the compound to be analyzed with a non-signal imidazole reagent to form an anion signal.

In one aspect, the invention features a class of non-signal imidazole reagents having the general structure of:

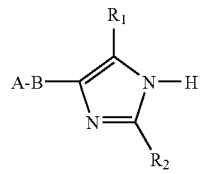

wherein either $R_1$ or $R_2$ is hydrogen (H) or deuterium (D), B comprises one to eight carbon atoms, A comprises an aryl group, and at least one of A or B is substituted with one or more atoms or groups other than H when A is phenyl and B comprises an amide group. In a preferred embodiment, B is substituted with four deuterium atoms and A is substituted with a bromine atom (Br), a chlorine atom (Cl), or one or more deuterium atoms. In other embodiments, A comprises a naphthyl or biphenyl group, or A is substituted with one or more fluorine atoms, alkyl groups or alkoxy groups; B comprises an amide group or an ether group. More preferably, B is $-CD_2CD_2-$ and A is $R_3C_6H_4CONH-$, wherein $R_3$ is Br or Cl.

One form of the invention features an isotopic duo non-signal imidazole reagent that ultimately yields two intense peaks for a signal phosphorimidazolide product. The isotopic duo reagent also can be used to compare the relative amounts of a phosphomonoester compound in two samples. The isotopic duo detection option can be practiced, for example, with natural bromoaryl non-signal imidazole reagents due to the high natural abundance of two stable isotopes of bromine. The same is true for corresponding chloroaryl imidazole reagents. The two-compound form of an isotopic duo non-signal imidazole reagent can consist of a mixture of corresponding enriched and non-enriched non-signal imidazole compounds in terms of enrichment with a stable isotope such as deuterium, in order to practice this invention.

In another aspect, the invention features a method for detecting phosphomonoester-containing compounds that includes the steps of providing a non-signal imidazole reagent, linking the reagent to the phosphomonoester compounds to form products that each provide a phosphorimidazolide anion signal group, and detecting these products as phosphorimidazolide anions by mass spectrometry. The reagent can be a mixture of two or more different non-signal imidazole reagents. The phosphomonoester-containing compound analyzed is, e.g., a nucleotide, dinucleotide or trinucleotide. Alternatively, the phosphomonoester-containing compound can be, e.g., a phosphopeptide. Preferably, the non-signal imidazole reagent contains an aryl group, and one of the adjacent carbon atoms of the imidazole group is substituted with a carbon atom. More preferably, the non-signal imidazole reagent is selected from the group consisting of N-[2-(1H-imidazol-4-yl)ethyl]benzamide, N-[2-(1H-imidazol-4-yl)ethyl-$d_4$]benzamide, 4-chloro-N-[2-(1H-imidazol-4-yl)ethyl]benzamide, 4-bromo-N-[2-(1H-imidazol-4-yl)ethyl]benzamide, and N-[2-(1H-imidazol-4-yl)ethyl]benz-$d_5$-amide. In the method, the product formed can be detected, e.g., by matrix-assisted laser desorption ionization mass spectrometry.

In a third aspect, the invention features aryl phosphorimidazolides having the general structure:

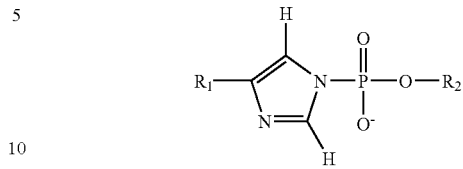

wherein $R_1$ comprises an aryl group and $R_2$ is an organic molecule. Preferably, $R_1$ comprises a phenyl group.

The method and compounds of the invention provide a host of advantages for the analysis of phosphomonoester-containing compounds, namely characteristic, multi-analyte detection with high sensitivity and specificity of known and unknown phosphomonoester-compounds simultaneously. Never before has it been possible to bring these advantages together in a single method for the analysis of phosphomonoester compounds.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings in which:

DETAILED DESCRIPTION OF THE INVENTION

Figure 1A:
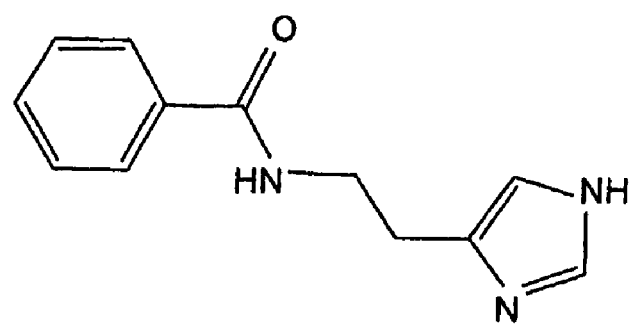
FIG. 1 shows exemplary non-signal imidazole reagents useful in the method of the invention.
Figure 1B:
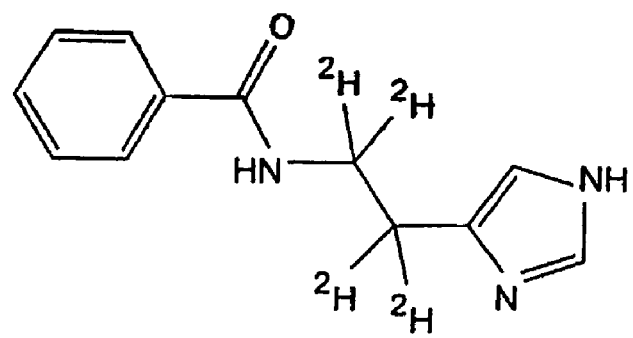
Figure 1C:
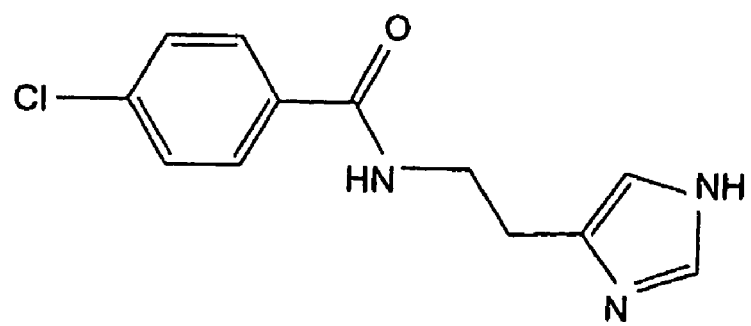
Figure 1D:
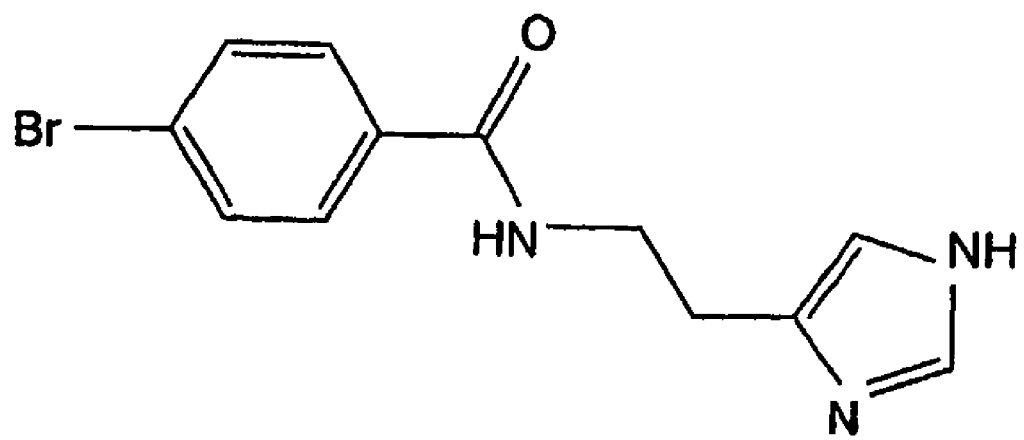
Figure 1E:
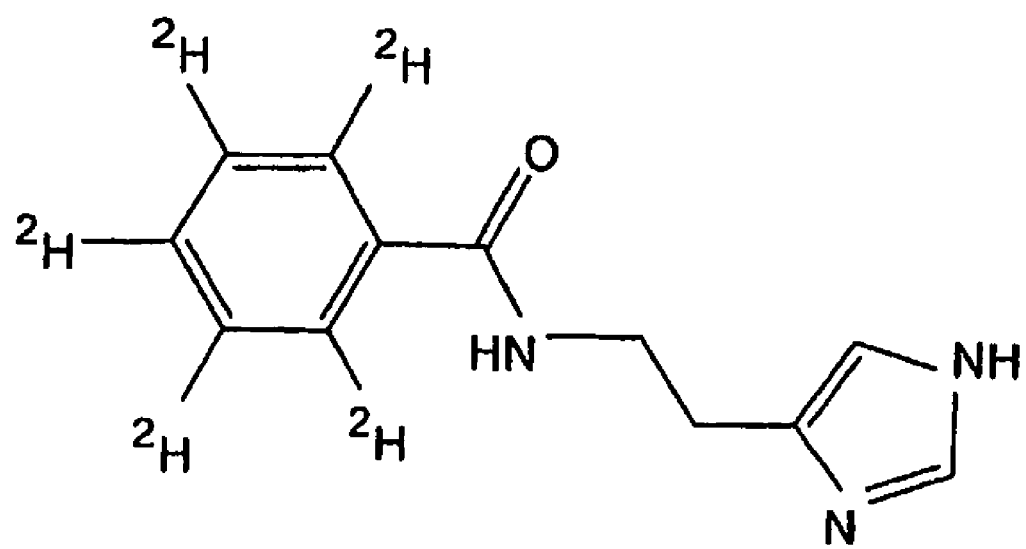

The method and compounds of the invention provide a host of advantages for the analysis of phosphomonoester-containing compounds, namely characteristic, multi-analyte detection with high sensitivity and specificity of known and unknown phosphomonoester-compounds simultaneously. The advantage of characteristic detection refers to the intact, complete molecular mass that the method of the invention can furnish for a phosphomonoester. The phosphorimidazolide anion signal group that is created in the linking step of this method enables the entire product from a phosphomonoester-containing compound to be detected as a molecular anion, thereby providing a characteristic detection. Because this invention can detect such products in this way with similar efficiency under a single set of conditions in the mass spectrometer, it also provides the advantage of multi-analyte detection for both known and unknown phosphomonoesters.

The advantage of high sensitivity is achieved by this invention through a combination of three critical properties. The first is that an intense signal group is created in the linking step between the phosphomonoester-containing compound and the non-signal imidazole reagent. When, instead, a pre-existing signal derivatization reagent is employed in a method, residual signal reagent, signal contaminants in this reagent, and reaction products of the signal reagent with nonanalyte compounds all can contribute to residual chemical noise at the end of the derivatization reaction. This reduces sensitivity, keeping in mind that sensitivity is signal over noise. It is very important for high sensitivity that a signal group is created as in the method of the invention rather than being pre-existing.

The second way in which this invention provides high sensitivity is that the phosphorimidazolide anion signal group is created with reagents that bear a positive charge or acquire a positive charge at low pH. This enables efficient removal of residual reagents at the end of the reaction in a simple way, such as by cation exchange chromatography. The third property of the invention that contributes to high sensitivity is that the phosphorimidazolide anion signal product that forms is both desorption-prone and fragmentation-resistant in the mass spectrometer. Often the phosphomonoester moiety is labile in the mass spectrometer, but this method stabilizes it. This leads to an intense peak for the molecular phosphorimidazolide anion of the product. The practice of the method of the invention with an aryl non-signal imidazole reagent and with MALDI-MS, such as MALDI-TOF-MS or MALDI-TOF/TOF-MS, is preferred for achieving high sensitivity based on the above three mechanisms for high sensitivity.

In addition to the fact that mass spectrometry is well-known as a specific technique in general, and that phosphorimidazolides can be formed specifically, additional specificity is achieved by this invention in two ways, both of which derive from the opportunity to employ a non-signal imidazole reagent as an isotopic duo. In the first technique, the relative amount of phosphomonoester-containing compounds can be compared in two samples by subjecting each sample to derivatization with only one member of the isotopic duo reagent. The samples then are combined for co-detection by mass spectrometry, where the relative peak heights for nonisotopic and isotopic forms of each phosphomonoester-containing compound provide the relative amounts of these compounds in each sample.

In the second strategy for boosting specificity, a given sample is labeled with a combined isotopic duo reagent, and peaks for the phosphomonoester-containing compounds can be discriminated against noise peaks, when the latter peaks are present in the mass spectrum, based on the isotopic mass spacing and relative peak heights for the pair of peaks from each derivatized phosphomonoester.

Phosphomonoester-containing compounds are at the heart of much biochemistry and physiology in both health and disease. The host of analytical advantages of this invention enables it to fill in gaps in understanding about the role of phosphomonoesters as bioactive agents, and in the ability of investigators to measure phosphomonoesters with high performance as biomarkers of health and disease. One example is metabolomics, the study of biological systems based on profiling many of the metabolites simultaneously. Generally, the initial goal is to discover the metabolic pathways that are disrupted in disease. Knowing these disruptions helps to find drugs that restore these pathways to normal and thereby treat the disease. This knowledge can also lead to discovery of metabolite analytes for clinical diagnostics. This invention enables phosphomonoester metabolites to be profiled.

A second example of an important application of this invention is the study of DNA damage by chemicals and radiation. Damage in this way to DNA is termed "DNA adducts." For more than, 30 years, cancer epidemiologists have wanted a good test for DNA adducts in people as a way to help individualize cancer prevention because DNA adducts contribute to the initiation of cancer. The concept is similar to the measurement of cholesterol to help individualize prevention of heart attacks. Unfortunately, in spite of thousands of research articles on DNA adducts, the trace amounts of DNA adducts in human samples (a million to a billion times less than level of cholesterol, requiring very sensitive detection techniques); the unknown structures of most of these adducts; the lack of a detection technique for discovering unknown DNA adducts in a specific way; and the limited ability of current methods to achieve multi-analyte detection with a relatively uniform response has stymied efforts to make the measurement of DNA adducts in humans a weapon against cancer. The method of the invention overcomes this barrier by providing the combination of key analytical properties that has been missing. The measurement of DNA adducts in people also is of interest because DNA adducts may contribute to aging, heart disease, infertility, and diabetes.

A third example of an important application of this invention is the measurement of phosphopeptides. The function of many proteins is controlled by phosphorylation. This takes place on the serine, theronine and tyrosine sites of proteins. Disruption of this phosphorylation takes place in many diseases. At the present time, the phosphorylation status of a protein generally is studied by digesting the protein to peptides, and measuring the phosphopeptides by mass spectrometry. Unfortunately, there are problems with sensitivity, specificity, uniform response and multi-analyte detection. This invention provides a way to overcome these problems and can be especially important in bringing some phosphopeptide assays into routine clinical diagnostics where high performance testing is of paramount importance.

A fourth example of an important application of this invention is in the analysis of phosphoinositides, a class of phosphomonoester-sugars that are broadly important in medicine and physiology. They are crucial regulators of nuclear functions, cytoskeletal dynamics, cell signaling and membrane trafficking.

A fifth example of an important application of this invention is its ability to discover previously unknown regulatory nucleotides in DNA. Such nucleotides (5-methylcytosine is a known example) would be formed biosynthetically (in contrast to formation of DNA adducts as a consequence of damage to DNA).

Materials and Methods for Synthesis

All chemicals were obtained from commercial suppliers and were used without further purification. NMR were recorded on Varian 300. MALDI-TOF-MS spectra were obtained on an Applied Biosystems Voyager-DE STR. Scintered glass funnels were used for filtrations. Stirring was done magnetically. Evaporations were done using a Rotary Evaporator. All ratios of solvents are volume:volume.

Synthesis: General Procedure:

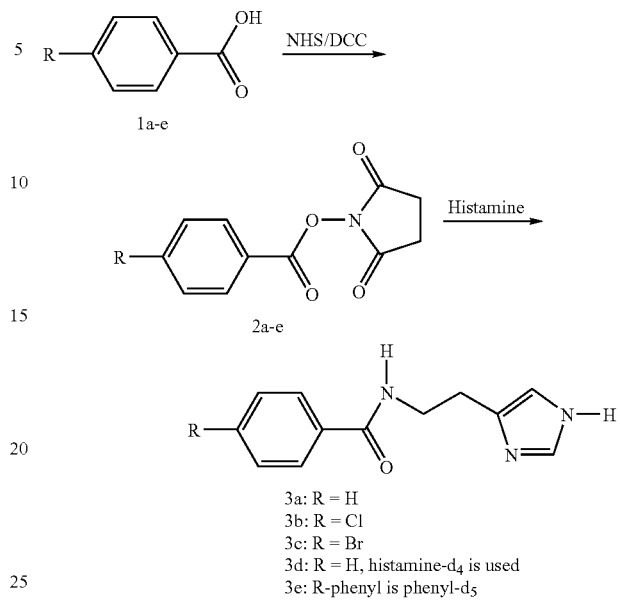

3a: R = H
3b: R = Cl
3c: R = Br
3d: R = H, histamine-$d_4$ is used
3e: R-phenyl is phenyl-$d_5$ Preparation of Imidazole Reagents (3): General Procedure.

One of compounds 1a-d was dissolved in tetrahydrofuran THF. One molar equivalent each of N-hydroxy succinimide (NHS) and 1,3-dicyclohexylcarbodiimide (DCC) were added, respectively. The mixture was stirred at room temperature (RT) for three hours. Dicyclohexylurea (DCU) was filtered off and the solvents were evaporated. The obtained N-hydroxy succinimide ester (one of 2a-d) was dried under vacuum and dissolved in acetonitrile. One equivalent of histamine dissolved in 50% acetonitrile/water and three equivalents of triethylamine were added, respectively. The mixture was stirred at room temperature for one hour. Solvents were evaporated and the residue was dried under vacuum and stirred in water. Solid compound (one of 3a-d) was filtered, washed with water and dried under vacuum. Compound 3e can be prepared similarly.

Synthesis of 3a as a Specific Example.

To 20 ml THF solution of 1.22 g (10 mmol) 1a, 1.18 g (10 mmol) NHS and 2.15 g (10 mmol) DCC were added. The mixture was stirred three hours at RT. DCU was filtered and solvents were evaporated. 2a was dried under vacuum. To 10 ml acetonitrile solution of 1.1 g (5 mmol) 2a, 580 mg histamine and 2.1 ml triethylamine in 10 ml acetonitrile/water (50/50, v/v) were added. The mixture was stirred at RT one hour. Solvents were evaporated, and the residue was further dried under vacuum and then suspended in 2 ml of water. After 15 min of stirring at RT, 3a was filtered, washed with 2 ml of cold water and dried under vacuum. The yield was 685 mg (63%).

Structural Characterization

2a: $^1$H NMR (ppm) in acetone-$d_6$: 2.96 (s, 4H), 7.6-7.7 (m, 2H), 7.75-7.84 (m, 1H), 8.1-8.2 (m, 2H).

2b: $^1$H NMR (ppm) in acetone-$d_6$: 2.97 (s, 4H), 7.65-7.75 (m, 2H), 8.10-8.18 (m, 2H).

2c: $^1$H NMR (ppm) in acetone-$d_6$: 2.97 (s, 4H), 7.84-7.9 (m, 2H), 8.0-8.1 (m, 2H).

3a: $^1$H NMR (ppm) in methanol-$d_4$: 2.89 (t, 2H, J=6.9 Hz), 3.61 (t, 2H, J=7.2 Hz), 6.86 (s, 1H), 7.39-7.55 (m, 3H), 7.59 (s, 1H), 7.74-7.80 (m, 2H).

3b: ¹H NMR (ppm) in methanol-$d_4$: 2.88 (t, 2H, J=7.2 Hz), 3.6 (t, 2H, J=7.2 Hz), 6.86 (s, 1H), 7.4-7.5 (m, 2H), 7.59 (s, 1H), 7.74-7.8 (m, 2H).

3c: ¹H NMR (ppm) in methanol-$d_4$: 2.88 (t, 2H, J=7.2 Hz), 3.6 (t, 2H, J=7.2 Hz), 6.86 (s, 1H), 7.55-7.64 (m, 2H), 7.66-7.72 (m, 2H).

3d: ¹H NMR (ppm) in methanol-$d_4$: 6.86 (s, 1H), 7.4-7.55 (m, 3H), 7.59 (s, 1H), 7.65-7.82 (m, 2H). MALDI/MS: $(M+H)^+=220.15$.

Materials and Methods for Analysis

CCA Matrix

Three mg of α-cyano-4-hydroxycinnamic acid (CCA, 47,687-0, Aldrich, Milwaukee, Wis.), were dissolved in 1.0 ml of acetonitrile:water, 1:1, followed by 1:10 dilution into methanol:water, 1:1, and immediate use. The methanol was from Fisher Scientific, Pittsburgh, Pa.

Settled Propylsulfonic Acid Silica (SPAS)

A 50-ml polypropylene test tube was charged with 20 g of propylsulfonic acid silica (JT Baker, Phillipsburg, N.J.) and 1 M $NH_4OH$ was added up to the 50-ml mark followed by shaking, settling, pouring off supernatant, and addition of more 1 M $NH_4OH$ (diluted from A669-500, 30%, Fisher Scientific, Pittsburgh, Pa. 15275) etc. until a pH of about 5 (pH paper) was reached. The supernatant was poured off, and the suspension was treated similarly with 0.01 M triethylammonium acetate (diluted from 1 M, 90359, Fluka, Industriestrasse 25, CH-9471 Buchs SG, Switzerland) until pH 7.0 is attained. The settled product in a total volume of 30 ml was kept unperturbed at 4° C. and used for at least four months.

Detection Procedure Variations

1. OASIS extraction of DNA adducts. After a sample of DNA was digested to nucleotides with nuclease P1 and phosphodiesterase I, and ultrafiltered (0.5 ml BIOMAX-5 Ultrafree-ML, Millipore, Bedford, Mass.) it was loaded onto an OASIS column (186000383, Waters, Milford, Mass.) that had been washed (gravity flow) once with 1.0 ml methanol and twice with 0.6 ml of 20 mM triethylammonium acetate, pH 7.0 (TEAA Solution). The sample was loaded followed by washing with 2×0.6 ml then 1 ml of TEAA Solution, followed by elution with 1.0 ml of 55% methanol in water into a 1.5 ml micro centrifuge tube (Fisher Scientific) and evaporation at room temperature in a Speed-Vac.

2a. Non-signal imidazole reagent labeling reaction (option for sample derived from step 1). Using an Eppendorf Reference 0.1-2.5 μL Pipettor (Brinkmann, Westbury, N.Y.), 2 μl each of 0.12 M 1-ethyl-3-[3-(dimethylamino)propyl]carbodiimide (EDC, dissolved in water and used within 5 min), and 4 μl of a 0.012 M non-signal imidazole reagent in acetonitrile:water, 1:1, were added to the above sample. After aspirating/dispensing the solution six times in order to mix it and also rinse down the sides of the tube, followed by capping, the reaction mixture was allowed to stand in the dark at room temperature for 2 h.

2b. Non-signal imidazole reagent labeling reaction (option for pre-dissolved sample of a phosphomonoester-containing compound). Using an Eppendorf Reference 0.1-2.5 μL Pipettor, 1 μl each of an organophosphate-containing sample in water, 0.12 M EDC (dissolved in water and used within 5 min), and 4 μl of a 0.012 M non-signal imidazole reagent in acetonitrile:water, 1:1, were combined in a 0.5 mL micro centrifuge tube (Fisher Scientific, Pittsburgh, Pa.). After capping, the reaction mixture was allowed to stand in the dark at room temperature for 2 h.

3. Ion exchange chromatography. Fifty μl of undisturbed SPAS was pipetted into an UltraMicroSpin Column (The Nest Group, Inc., Southborough, Mass.), followed by spinning in Micro-Centrifuge Model 59A (Fisher Scientific) at Speed 8 for 10 sec. After similar pipetting and spinning of 2×65 μl of methanol:water, 35:65, the above reaction mixture was applied onto the center of the ion exchanger and spun into a collection PCR tube (0.2 mL thin-wall PCR tube, 67103-60, Cole Parmer, Vernon Hills, Ill.) followed similarly by 5 μL of methanol:water 35:65. The PCR tube was placed into a 1.5 mL micro centrifuge tube (05-406-17, Fisher Scientific) and its solution was taken to dryness at room temperature in a Speed-Vac (~15 min), followed by dissolving in 5 μL of acetonitrile:methanol:TEAA Solution (6.5:6.5:87).

4a. C18 solid phase extraction (first option for step 4). After a ZipTip C18 pipette tip was conditioned by aspirating/dispensing 3×10 μl of methanol and 5×10 μl of water with a 10 μl Eppendorf Pipettor, the above redissolved sample (in 10 μL of ACN:TEAA solution, 2:98) was aspirated/dispensed five times (rimming the pipette tip during dispensing at the bottom of the PCR tube up to the 10 μl level) followed by aspirating/dispensing 5×10 μl of 0.02 M pH 7 triethylammonium acetate. Elution of the pipette tip onto a MALDI plate was accomplished as described (http://www.millipore.com/publications.nsf/docs/PS2342ENUS) by using a 10-μl HPLC syringe (80365, Hamilton, Reno, Nev.,) to deliver 3 μl each of 5, 10, 20, 30, 50, and 75% methanol in water through the ZipTip, with each 0.5 μl of eluent spotted onto a new well of a MALDI plate (384 well plate with hydrophobic plastic surface, 4327695, Applied Biosystems, Foster City, Calif.), followed by air-drying for 5 min prior to step 5.

4b. CapLC column switching (second option for step 4). The sample solution was injected into a C18-Si trapping column (300 μm id×5 mm, C18, 5 μm, 10A) of a column switching module in a nano-LC system (LC Packings, Dionex Corporation, Sunnyvale Calif.). After washing with TEAA Solution:acetonitrile, 99:1 (to retain more polar nucleotides), or 97:3 (to remove more of the normal nucleotides) for 3 min at 25 μl/min, switching was done to direct a reverse flow of TEAA Solution:acetonitrile:methanol, 90:5:5 (10% organic) onto a micro column (180 μm I.D., 15 cm length, C18-Si, 5 μm, 100 A), and elution was done with 10 to 35% organic in 0.1×TEAA Solution (2.0 mM) over 7 min, at 2.0 μl/min with automated collection of droplets onto a hydrophobic-coated MALDI plate for 20 sec each using a Probot Micro Fraction Collector (LC Packings, Dionex Corporation), followed by 35% organic for 16 min, 35 to 70% organic over 1 min, and 70% organic for 20 min.

5. MALDI-TOF analysis. Onto each dried spot from step 4 was applied 0.5 μl of CCA matrix. After air-drying for 5 min, the spots on the MALDI plate were analyzed in a MALDI-TOF mass spectrometer (Voyager-DE STR, Applied Biosystems, Foster City, Calif.) in the negative ion mode. Usually the data from 50 but up to 200 laser shots (3 Hz) were accumulated to yield a final mass spectrum, at a relative intensity setting for the nitrogen laser such as 2100. Reflectron mode: grid at 68%, source delay time 200 nsec. Linear mode: grid at 94.2%, source delay time 230 nsec.

The structures of some non-signal imidazole reagents that can be used to practice the invention are shown in FIG. 1. A non-signal imidazole reagent consists, e.g., of one or more of these compounds. Compound 1 is N-[2-(1H-imidazol-4-yl)ethyl]benzamide, 2 is N-[2-(1H-imidazol-4-yl)ethyl-$d_4$]benzamide, 3 is 4-chloro-N-[2-(1H-imidazol-4-yl)ethyl]benzamide, 4 is 4-bromo-N-[2-(1H-imidazol-4-yl)ethyl]benzamide, and 5 is N-[2-(1H-imidazol-4-yl)ethyl]benz-$d_5$-amide. Examples of isotopic duo non-signal imidazole reagents useful in the mass splitting option of this invention are as follows: 1+2, 1+5, 2+4, and 3+4.

Figure 2:
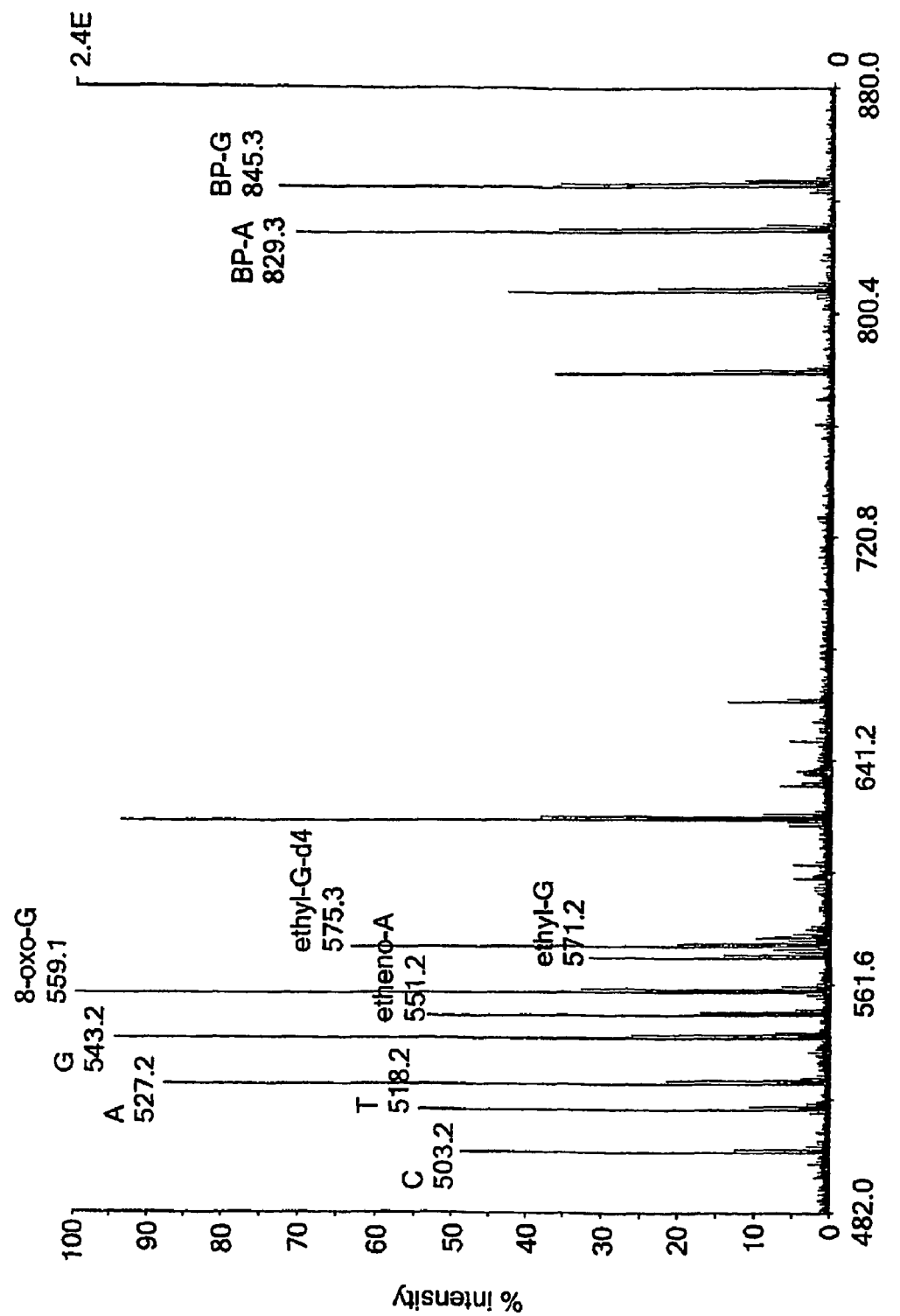
FIG. 2 shows detection of deoxynucleotides labeled with a non-signal imidazole reagent according to the method of the invention.

In FIG. 2 is shown the simultaneous detection of 50 fmol each of nine nucleotides that have been labeled with compound 1. These nine deoxynucleotides are the four normal deoxynucleotides and the five DNA adducts $N^2$-ethyl-G, 1,$N^6$-etheno-A, 8-oxo-G, benzo[a]pyrene-A, benzo[a]pyrene-G, and $N^2$-ethyl-$d_4$-G, where the G represents dGMP and the A represents dAMP.

Figure 3:
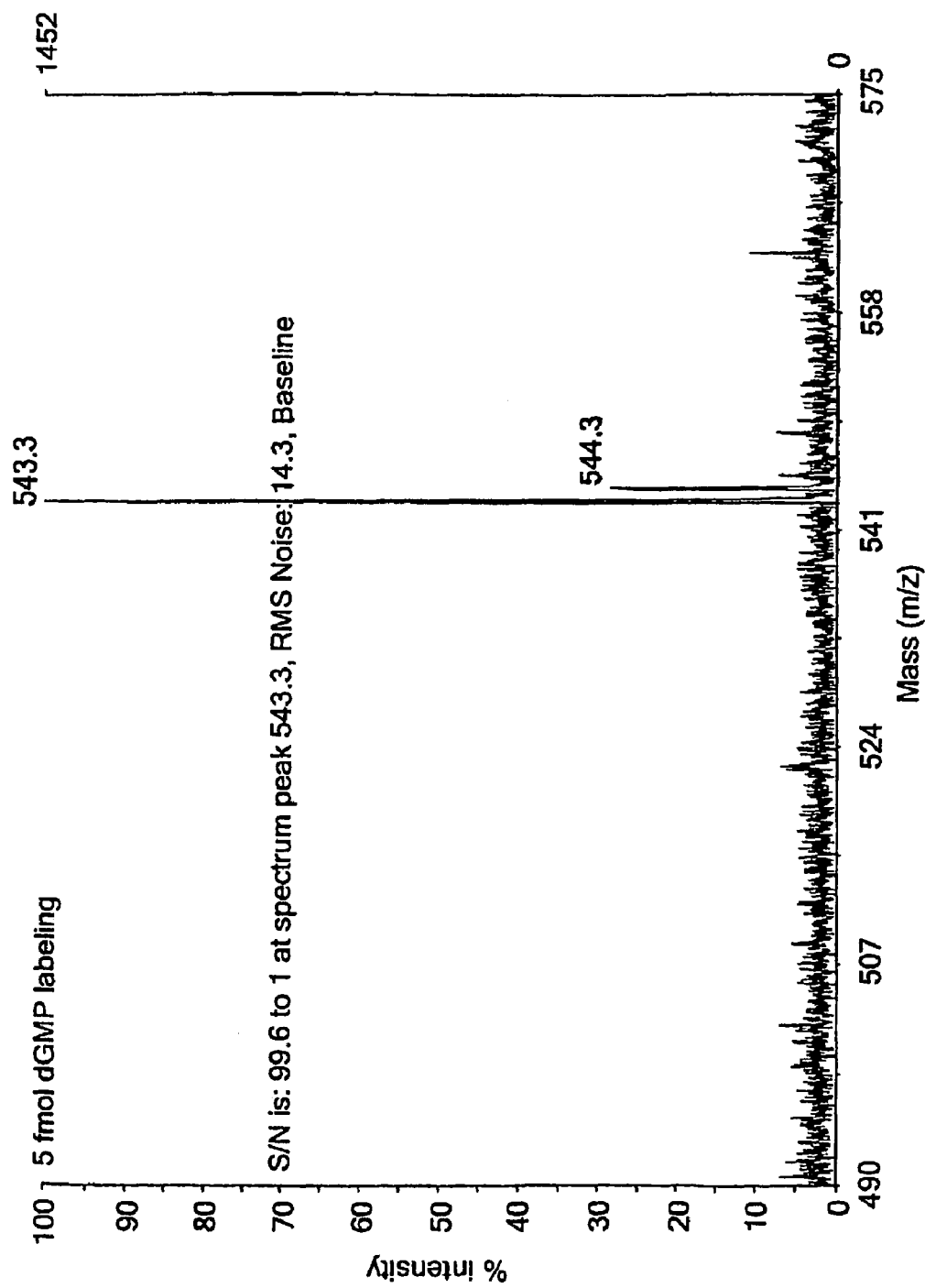
FIG. 3 shows detection of 5 fmol of a deoxynucleotide with the method of the invention.

5'-Deoxyguanosine monophosphate (5'-dGMP) was successfully detected starting with 5 fmol of this compound. In this case option 4b rather than 4a was used in the method of the invention. The MALDI-TOF-MS spectrum obtained is shown in FIG. 3, where a signal to noise ratio of 100 is seen.

Figure 4:
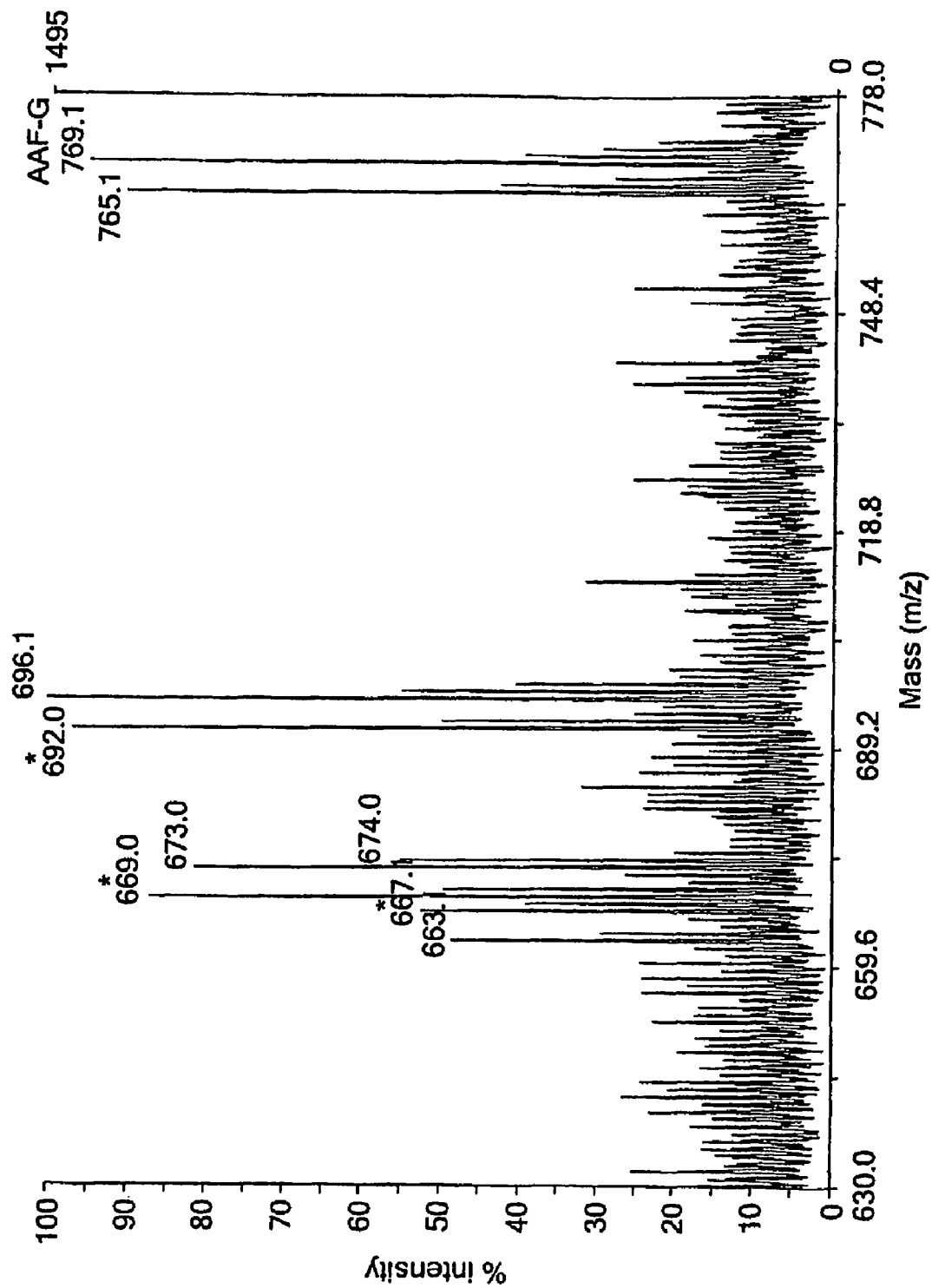
FIG. 4 shows the detection, with the method of the invention of an acetylaminofluorene DNA adduct spiked into DNA.

Use of an isotopic duo non-signal imidazole reagent comprising compounds 1 and 2 is shown in FIG. 4. In the experiment leading to this MALDI-TOF-MS spectrum, 100 fmol of an acetylaminofluorene dGMP DNA adduct (AAF-G) was spiked into 300 μg of digested calf thymus DNA after step 1. The AAF-G is detected as a pair of peaks at m/z 765.1 and m/z 769.1. Also seen in this mass spectrum are peak pairs for three unknown phosphomonoesters in calf thymus DNA that are marked by stars.

Figure 5:
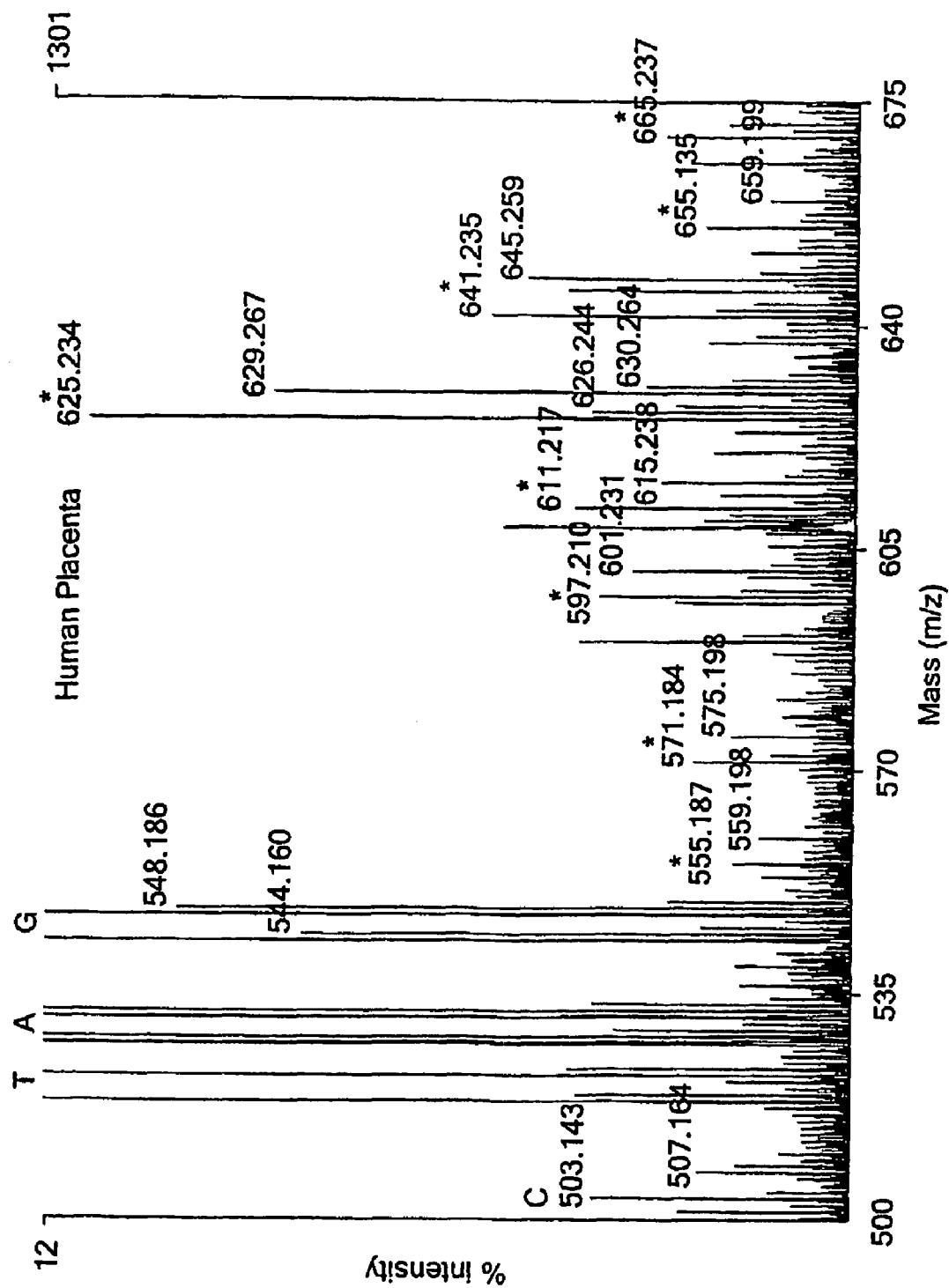
FIG. 5 shows the detection, with the method of the invention, of the four common deoxynucleotides of DNA, dimethyldeoxyadenosine monophosphate (tentatively identified), and unknown phosphomonoesters when the method was applied to DNA from human placenta.

DNA from human placenta was subjected to the method of the invention with option 4a using an isotopic duo non-signal imidazole reagent consisting of compounds 1 and 2. This led to the mass spectrum shown in FIG. 5. Along with the four normal deoxynucleotides, unknown phosphomonoesters are detected. The pair of peaks at m/z 571.184 and 575.198 correspond to a phosphorimidazolide isotopic duo of dimethyladenosine monophosphate, suggesting that the DNA sample was contaminated by RNA.

Figure 6:
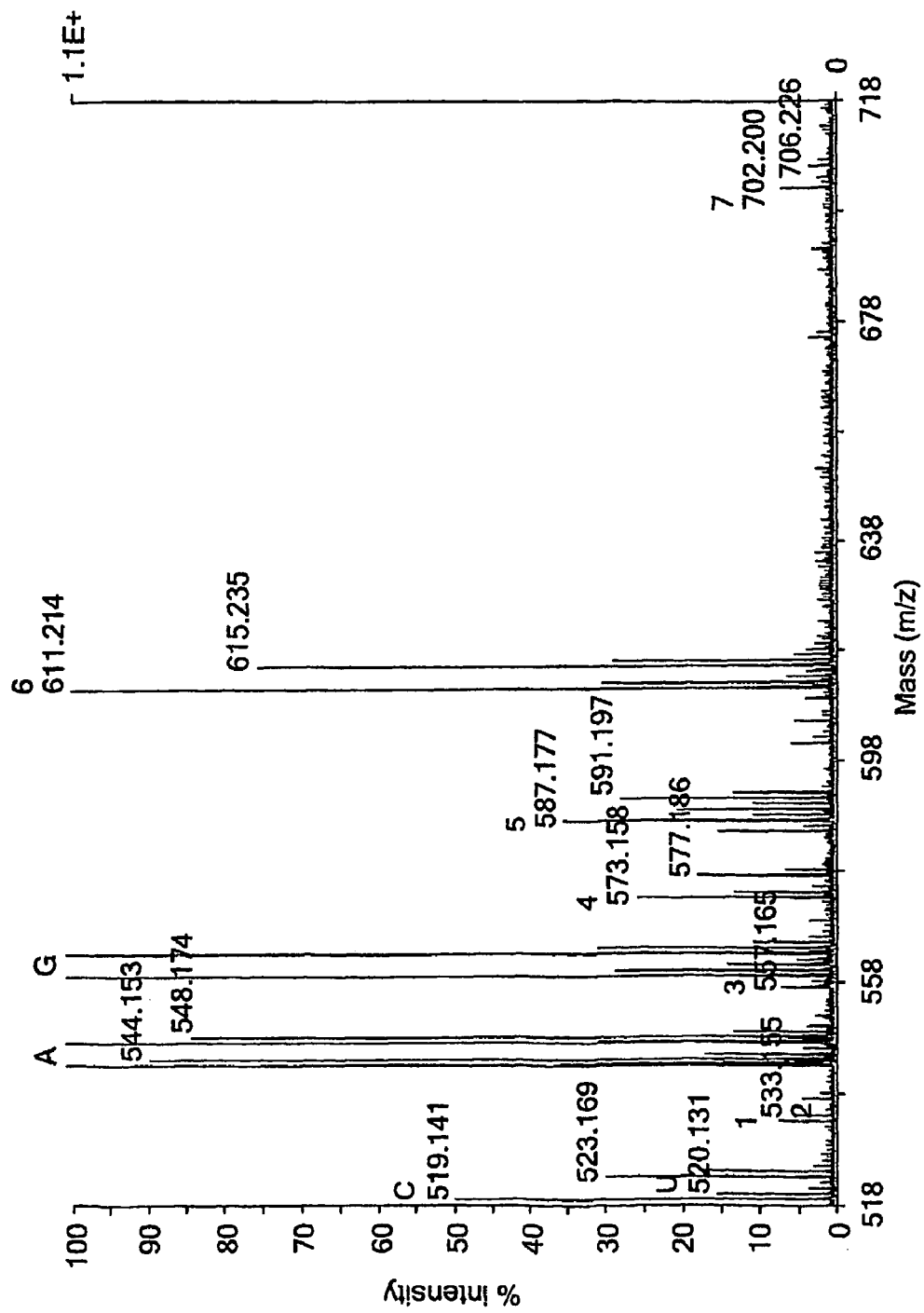
FIG. 6 shows the detection of ribonucleotides from transfer RNA using the method of the invention.

The detection of ribonucleotides from transfer RNA is shown in FIG. 6. 300 μg of tRNA, phenylalanine specific from brewers yeast (R4018, Sigma, St Louis, Mo. 63118) was digested to nucleotides with nuclease P1 and subjected to steps 2-5 of the method according to the invention using option 4a.

Peak Assignments in FIG. 6
1. 3-methyl-C, 5-methyl-C, 2'-O-methyl-C
2. 5-methyl-U, 2'-O-methyl-U, 1-methylpseudo-U, 2'-O-methylpseudo-U
3. 1-methyl-A, 2-methyl-A, $N^6$-methyl-A, 2'-O-methyl-A
4. 1-methyl-G, $N^2$-methyl-G, 7-methyl-G, 2'-O-methyl-G
5. $N^2,N^2$-dimethyl-G, $N^2,2'$-O-dimethyl-G, 7-aminomethyl-7-deaza-G, 1,2'-O-dimethyl-G
6. $N^6$-isopentenyl-A
7. $N^6$-methyl-$N^6$-threonylcarbamoyladesosine, $N^6$-hydroxynorvalylcarbamoyladenosine Other possible modified nucleotide ions include: pseudo-U (m/z at 520), dihydro-U (522), 2-thio-C (535), inosine (544), $N^4$-acetyl-C (561), 5-formyl-2'-O-methyl-C (561), $N^4$-acetyl-2'-O-methyl-C (575).

Figure 7:
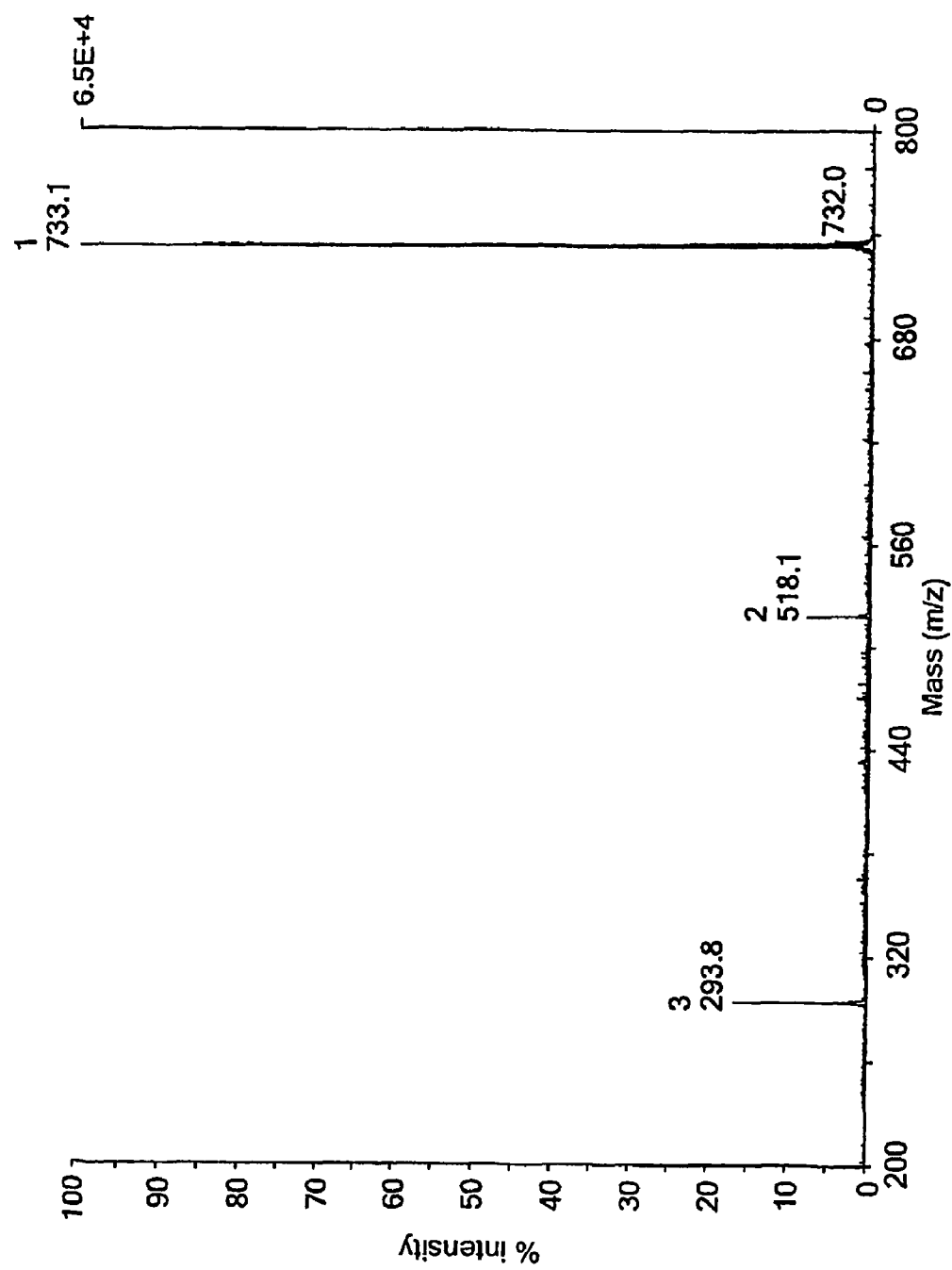
FIG. 7 shows the detection of a phosphopeptide using the method of the invention.

FIG. 7 shows the detection of a phosphopeptide based on labeling with a non-signal imidazole reagent consisting of compound 1. The sequence of this pentapeptide is gly-gln-phosphotyr-gly-lys.

Figure 8:
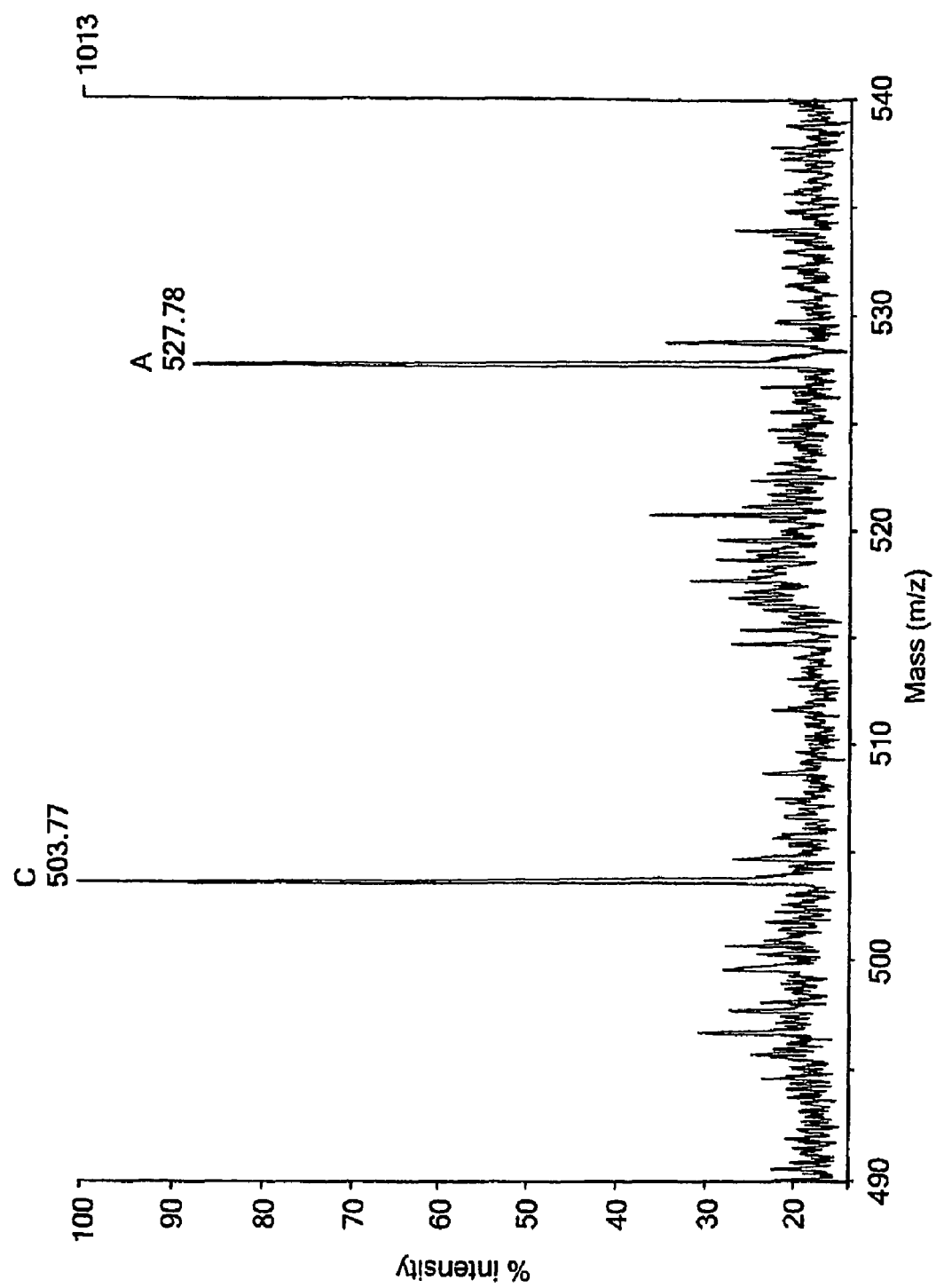
FIG. 8 shows detection at the amol level using the method of the invention.

5'-Deoxycytidine monophosphate and 5'-deoxyadenosine monophosphate, as derivatives with a non-signal imidazole reagent consisting of compound 1, were detected in 150 amol amounts applied to a MALDI target as shown in FIG. 8.

Figure 9:
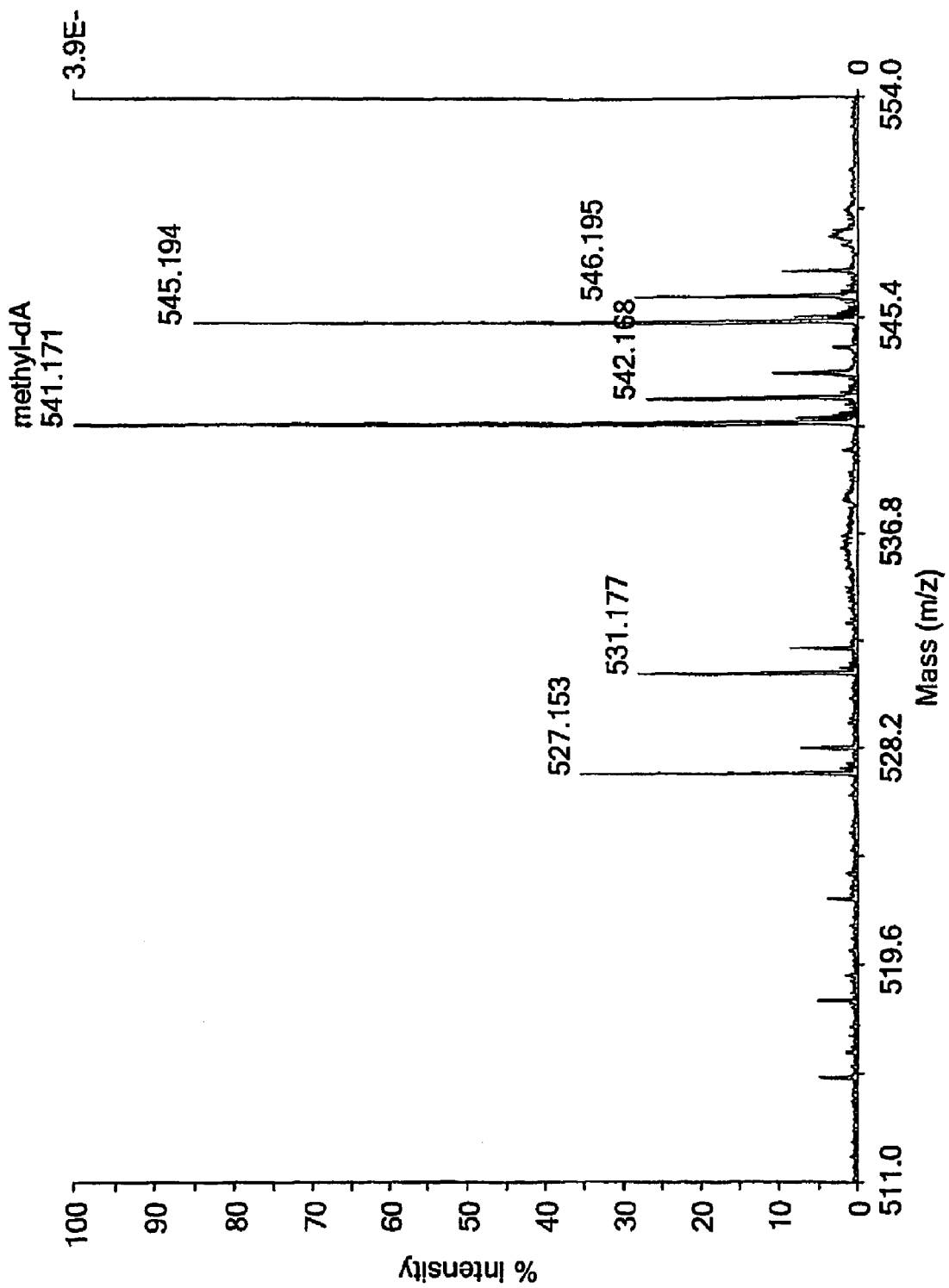
FIG. 9 shows direct evidence of $N^6$ MedA in mammalian DNA.

The power of the method is further illustrated by its ability to provide the first direct evidence for N6-methyladenine as a natural component of mammalian DNA. Many years of testing by many techniques, including many forms of mass spectrometry, have failed to make this discovery. In contrast, detection of this modified nucleotide in mammalian DNA is easy by the method of the invention, as shown in FIG. 9. Indeed, in a recent review of the subject (Ratel D., Ravanat, J.-L., Berger, F., Wion, D., 2006, N6-methyladenine: the other methylated base of DNA, BioEssays 28: 309-315), it was stated, "Furthermore, indirect evidence suggests the presence of m6A in mammal DNA, raising the possibility that this base has remained undetected due to the low sensitivity of the analytical methods used. This highlights the importance of considering m6A as the sixth element of DNA."

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method for detecting a phosphomonoester-containing compound, said method comprising the steps of:
providing a sample to be assayed for the presence of a phosphomonoester-containing compound;
providing a non-signal imidazole reagent, said reagent having the structure:

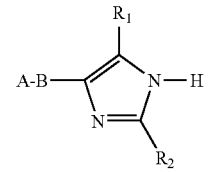

wherein either $R_1$ or $R_2$ is hydrogen (H) or deuterium (D), B comprises one to eight carbon atoms, A comprises an aryl group, and at least one of A or B is substituted with one or more atoms or groups other than H when A is phenyl and B comprises an amide group; and wherein the imidazole reagent has no ionic group;
combining said sample and said non-signal imidazole reagent, wherein said non-signal imidazole reagent forms a product comprising a phosphorimidazolide anion signal group with any reactable phosphomonoester-containing compound in said sample; and
detecting said product as a phosphorimidazolide anion by mass spectrometry.

2. The method of claim 1, wherein said reagent comprises a mixture of two or more different non-signal imidazole reagents.

3. The method of claim 1, wherein said phosphomonoester-containing compound is a nucleotide, dinucleotide or trinucleotide.

4. The method of claim 1, wherein said phosphomonoester-containing compound is a phosphopeptide.

5. The method of claim 1, wherein said non-signal imidazole reagent is N-[2-(1H-imidazol-4-yl)ethyl]benzamide.

6. The method of claim 1, wherein said non-signal imidazole reagent is selected from the group consisting of N-[2-(1H-imidazol-4-yl)ethyl-$d_4$]benzamide, 4-chloro-N-[2-(1H-imidazol-4-yl)ethyl]benzamide, 4-bromo-N-[2-(1H-imidazol-4-yl)ethyl]benzamide, and N-[2-(1H-imidazol-,4-yl)ethyl]benz-$d_5$-amide.

7. The method of claim 1, wherein said product is detected by matrix-assisted laser desorption ionization mass spectrometry.

8. The method of claim 1, wherein B is substituted with four deuterium atoms.

9. The method of claim 1, wherein A is substituted with a bromine atom (Br), a chlorine atom (Cl), or one or more deuterium atoms.

10. The method of claim 1, wherein A comprises a naphthyl or biphenyl group.

11. The method of claim 1, wherein A is substituted with one or more fluorine atoms, alkyl groups or alkoxy groups.

12. The method of claim 1, wherein B comprises an amide group or an ether group.

13. The method of claim 1, wherein B is —$CD_2CD_2$— and A is $R_3C_6H_4CONH$—, wherein $R_3$ is Br or Cl.

* * * * *